United States Patent
Hendrickson et al.

(10) Patent No.: US 9,532,847 B2
(45) Date of Patent: Jan. 3, 2017

(54) MEDICAL DEVICE PACKAGE

(71) Applicant: GT UROLOGICAL, LLC, Minneapolis, MN (US)

(72) Inventors: David L. Hendrickson, Coon Rapids, MN (US); David W. Anderson, Brooklyn Park, MN (US)

(73) Assignee: GT Urological, LLC, Minneapolis, MN (US)

( * ) Notice: Subject to any disclaimer, the term of this patent is extended or adjusted under 35 U.S.C. 154(b) by 201 days.

(21) Appl. No.: 14/333,384

(22) Filed: Jul. 16, 2014

(65) Prior Publication Data

US 2015/0021221 A1 Jan. 22, 2015

Related U.S. Application Data

(60) Provisional application No. 61/957,928, filed on Jul. 16, 2013.

(51) Int. Cl.
*A61J 1/00* (2006.01)

(52) U.S. Cl.
CPC ............... *A61B 50/33* (2016.02); *A61B 50/20* (2016.02); *A61B 50/30* (2016.02); *A61B 2050/005* (2016.02); *A61B 2050/0065* (2016.02); *A61B 2050/3006* (2016.02)

(58) Field of Classification Search
CPC ............ A61B 19/0256; A61B 19/0271; A61B 19/026
USPC ...... 206/438, 363, 370, 364; 220/254.3, 837
See application file for complete search history.

(56) References Cited

U.S. PATENT DOCUMENTS

| | | | | |
|---|---|---|---|---|
| 2,562,609 | A * | 7/1951 | Frohnapel | F25D 23/026 220/215 |
| 2,955,705 | A * | 10/1960 | Krueger, Sr. | A61B 19/026 206/365 |
| 3,249,070 | A * | 5/1966 | Day | A61B 19/0271 108/26 |
| 3,802,555 | A * | 4/1974 | Grasty | A61B 19/026 206/370 |
| 3,851,649 | A * | 12/1974 | Villari | A61M 25/002 206/223 |

(Continued)

OTHER PUBLICATIONS

International search report for international application No. PCT/US2014/046898, dated Nov. 26, 2014 (3 pages).

(Continued)

*Primary Examiner* — King M Chu
(74) *Attorney, Agent, or Firm* — Hamre, Schumann, Mueller & Larson, P.C.

(57) ABSTRACT

A package system for a medical device is disclosed. The package system may include a first part and a second part, where a holding platform can be incorporated into the first part of the package system and a collection tray can be incorporated into the second part of the package system. The first part may include leg portions. The leg portions of the first part can be folded and fitted into matching pockets of the second part, so that the first part of the package system can provided a relatively elevated and stable holding platform to hold the medical device. The package system can contain the medical device in the package system in a storage state, and hold the medical device with the holding platform in an application state.

14 Claims, 5 Drawing Sheets

(56) References Cited

U.S. PATENT DOCUMENTS

| | | | | |
|---|---|---|---|---|
| 3,983,996 A * | 10/1976 | Hendren, III | A61M 25/002 | 206/363 |
| 4,043,754 A * | 8/1977 | Sklar | A61L 2/26 | 206/370 |
| 4,065,816 A * | 1/1978 | Sawyer | A61F 2/2427 | 206/438 |
| 4,135,868 A * | 1/1979 | Schainholz | A61L 2/26 | 206/438 |
| 4,143,695 A * | 3/1979 | Hoehn | A45C 11/20 | 220/215 |
| 4,226,328 A * | 10/1980 | Beddow | A61M 25/002 | 206/364 |
| 4,269,315 A * | 5/1981 | Boyce | B65D 83/0847 | 128/206.19 |
| 4,314,637 A * | 2/1982 | Posso | G11B 23/0233 | 206/1.5 |
| 4,366,915 A * | 1/1983 | Seidler | A45C 11/24 | 206/1.5 |
| 4,408,692 A * | 10/1983 | Sigel | A61B 1/00144 | 206/303 |
| 4,545,783 A * | 10/1985 | Vaughan | A61J 1/00 | 206/364 |
| 4,595,102 A * | 6/1986 | Cianci | A61B 19/0271 | 206/370 |
| 4,643,303 A * | 2/1987 | Arp | A61L 2/26 | 206/370 |
| 4,730,729 A * | 3/1988 | Monch | A61B 1/121 | 206/363 |
| 4,736,850 A * | 4/1988 | Bowman | A61F 2/062 | 206/370 |
| 4,820,306 A * | 4/1989 | Gorman | A61B 17/8816 | 128/898 |
| 4,842,138 A * | 6/1989 | Sandel | | 206/363 |
| 4,921,096 A * | 5/1990 | McFarlane | A61M 25/002 | 206/349 |
| 4,928,830 A * | 5/1990 | Brewer | A61B 19/026 | 206/363 |
| 4,989,733 A * | 2/1991 | Patry | A61B 19/0271 | 206/210 |
| 5,002,197 A * | 3/1991 | Ponsi | B65D 43/161 | 220/255 |
| 5,027,999 A * | 7/1991 | Kucherer | B65D 43/161 | 220/270 |
| 5,031,768 A * | 7/1991 | Fischer | A61B 19/0264 | 206/364 |
| 5,038,938 A * | 8/1991 | Berndt | A61M 1/0096 | 206/365 |
| 5,046,608 A * | 9/1991 | Laipply | A47K 10/16 | 206/209 |
| 5,064,088 A * | 11/1991 | Steffes | A45C 11/20 | 220/837 |
| 5,080,225 A * | 1/1992 | Russo | A61B 10/0096 | 206/204 |
| 5,085,331 A * | 2/1992 | Groya | B65D 47/0847 | 215/235 |
| 5,148,920 A * | 9/1992 | Walker | B65D 81/1075 | 206/438 |
| 5,165,387 A * | 11/1992 | Woodson | A61B 1/0669 | 206/438 |
| 5,176,258 A * | 1/1993 | Antal | B65D 75/326 | 206/438 |
| 5,178,282 A * | 1/1993 | Williams | | 206/363 |
| 5,193,679 A * | 3/1993 | White | A61F 2/0095 | 206/363 |
| 5,246,109 A * | 9/1993 | Markle | A61B 5/145 | 206/363 |
| 5,281,400 A * | 1/1994 | Berry, Jr. | A61L 2/26 | 206/363 |
| 5,284,632 A * | 2/1994 | Kudla | A61B 19/0271 | 206/263 |
| 5,301,807 A * | 4/1994 | Donahue | A45C 11/24 | 206/363 |
| 5,337,911 A * | 8/1994 | Holub | A45C 11/20 | 16/383 |
| 5,339,955 A * | 8/1994 | Horan | A61B 19/0271 | 206/350 |
| 5,392,918 A * | 2/1995 | Harrison | A61B 19/026 | 206/364 |
| 5,413,217 A * | 5/1995 | Sauer | B65D 77/0433 | 206/363 |
| 5,441,707 A * | 8/1995 | Lewis | A61L 2/26 | 206/438 |
| 5,485,917 A * | 1/1996 | Early | A61B 19/026 | 206/363 |
| 5,772,031 A * | 6/1998 | Landis | A61B 19/026 | 206/363 |
| 5,842,567 A * | 12/1998 | Rowe | A61B 19/0262 | 206/364 |
| 5,884,800 A * | 3/1999 | Hall | B65D 25/16 | 220/495.03 |
| 5,927,535 A * | 7/1999 | Goth | B65D 47/0847 | 220/254.3 |
| 5,947,284 A * | 9/1999 | Foster | A61B 19/026 | 206/364 |
| 5,984,097 A * | 11/1999 | Kalinski | A61B 17/06114 | 206/366 |
| 6,000,548 A * | 12/1999 | Tsals | A61M 5/002 | 206/438 |
| 6,012,578 A * | 1/2000 | Keilman | A61M 1/28 | 206/438 |
| 6,012,580 A * | 1/2000 | Peters | B65D 75/58 | 206/438 |
| 6,012,586 A * | 1/2000 | Misra | | 206/370 |
| 6,039,183 A * | 3/2000 | Rudnick | A61F 2/0095 | 206/438 |
| 6,059,111 A * | 5/2000 | Davila | B65D 5/5028 | 206/438 |
| 6,068,121 A * | 5/2000 | McGlinch | A61M 25/002 | 206/364 |
| 6,311,838 B1 * | 11/2001 | Johnson | B25H 3/021 | 206/363 |
| 6,412,637 B1 * | 7/2002 | Saunders | B65D 1/36 | 206/459.1 |
| 6,460,718 B1 * | 10/2002 | Vogel | B65D 21/0219 | 206/508 |
| 6,471,083 B1 * | 10/2002 | Helms | B65D 43/161 | 220/254.3 |
| 6,534,000 B1 * | 3/2003 | Michaelson | A61C 19/002 | 206/363 |
| 6,821,286 B1 * | 11/2004 | Carranza | A61B 19/026 | 606/151 |
| 6,884,392 B2 * | 4/2005 | Malkin | A61B 1/123 | 134/198 |
| 6,889,839 B1 * | 5/2005 | Rosten | B65D 81/075 | 206/363 |
| 6,915,901 B2 * | 7/2005 | Feinberg | A61B 17/00491 | 206/363 |
| 6,991,096 B2 * | 1/2006 | Gottlieb | A61B 19/026 | 206/210 |
| 7,159,716 B2 * | 1/2007 | Ashby | B26F 1/12 | 206/438 |
| D543,030 S * | 5/2007 | Schafer | D3/272 | |
| 7,258,233 B2 * | 8/2007 | Lee | B65D 43/161 | 206/470 |
| 7,802,681 B2 * | 9/2010 | Williams | A61B 17/43 | 206/363 |
| 7,886,927 B2 * | 2/2011 | Frey | B65D 47/0847 | 220/254.3 |
| 8,006,839 B2 * | 8/2011 | Hafner | A61B 19/026 | 206/363 |
| 8,132,690 B2 * | 3/2012 | Hall | B65D 47/0847 | 220/254.3 |
| 8,240,468 B2 * | 8/2012 | Wilkinson | A61B 5/417 | 206/363 |
| 8,517,212 B2 * | 8/2013 | Antal, Sr. | B65D 43/161 | 220/254.3 |
| 8,753,363 B2 * | 6/2014 | Anderson | A61F 2/0036 | 600/30 |

(56) References Cited

U.S. PATENT DOCUMENTS

| | | | | |
|---|---|---|---|---|
| 2002/0014430 A1* | 2/2002 | Groth | A61M 5/002 | 206/438 |
| 2002/0053528 A1* | 5/2002 | Johnson | B25H 3/021 | 206/363 |
| 2002/0070218 A1* | 6/2002 | Mozes | B65D 43/161 | 220/254.3 |
| 2002/0112981 A1* | 8/2002 | Cooper | A61B 19/026 | 206/438 |
| 2002/0185406 A1* | 12/2002 | Massengale | A61B 19/026 | 206/571 |
| 2003/0042170 A1* | 3/2003 | Bolanos | A61B 10/0096 | 206/570 |
| 2003/0062281 A1* | 4/2003 | Giard, Jr. | A61B 5/14 | 206/364 |
| 2003/0121810 A1* | 7/2003 | Roshdy | B65D 1/36 | 206/363 |
| 2004/0195131 A1* | 10/2004 | Spolidoro | A61B 19/026 | 206/438 |
| 2005/0016886 A1* | 1/2005 | Riley | A61B 19/0256 | 206/438 |
| 2005/0077197 A1* | 4/2005 | Detruit | A61F 2/0095 | 206/363 |
| 2005/0087464 A1* | 4/2005 | Brattesani | B65D 75/54 | 206/361 |
| 2005/0098460 A1* | 5/2005 | Smith | A61B 19/026 | 206/366 |
| 2005/0115869 A1* | 6/2005 | Maffei | A61F 15/001 | 206/775 |
| 2006/0273084 A1* | 12/2006 | Baker | A61B 19/026 | 220/23.4 |
| 2006/0282045 A1* | 12/2006 | Wilkinson | A61B 5/1405 | 604/198 |
| 2007/0000802 A1* | 1/2007 | Keller | A61F 2/0095 | 206/438 |
| 2007/0084742 A1* | 4/2007 | Miller | A61B 17/3472 | 206/438 |
| 2007/0185495 A1* | 8/2007 | Hess | A61M 5/008 | 606/93 |
| 2008/0045857 A1* | 2/2008 | Miller | A61B 10/025 | 600/566 |
| 2008/0125721 A1* | 5/2008 | Timm | A61K 9/0048 | 604/187 |
| 2009/0194446 A1* | 8/2009 | Miller | A61B 10/025 | 206/438 |
| 2009/0301927 A1* | 12/2009 | Fvlbrook | A61B 19/0271 | 206/564 |
| 2010/0219092 A1* | 9/2010 | Salahieh | A61F 2/0095 | 206/438 |
| 2010/0307941 A1* | 12/2010 | Tomes | A61M 25/00 | 206/366 |
| 2011/0071572 A1* | 3/2011 | Sixto | A61B 17/8875 | 606/286 |
| 2011/0186456 A1* | 8/2011 | Bertazzoni | 206/438 | |
| 2011/0218502 A1* | 9/2011 | Iio | A61M 5/003 | 604/264 |
| 2011/0226652 A1* | 9/2011 | Hickmott | A61M 5/14248 | 206/438 |
| 2011/0232234 A1* | 9/2011 | Lockwood | A61M 25/00 | 53/443 |
| 2011/0278188 A1* | 11/2011 | Steinhardt | A61F 2/0095 | 206/438 |
| 2012/0191203 A1* | 7/2012 | Liccardo | A61F 2/0095 | 623/19.11 |
| 2013/0284629 A1* | 10/2013 | Kinyon | A61F 2/0095 | 206/438 |
| 2014/0360903 A1* | 12/2014 | Iio | A61M 5/002 | 206/364 |

OTHER PUBLICATIONS

Written Opinion for international application No. PCT/US2014/046898, dated Nov. 26, 2014 (6 pages).

* cited by examiner

MEDICAL DEVICE PACKAGE

FIELD

The disclosure herein relates to systems, methods and apparatuses of packaging a medical device. More specifically, the disclosure herein relates to systems, methods and apparatuses to package a medical device, such as a medical device that may require filling with liquid before an application of the medical device.

BACKGROUND

Some medical devices, including for example vessel occlusive devices (e.g. artificial urinary, bowel or esophageal sphincters), tissue expanders, or breast implant, may require some parts to be filled with liquids for proper operation. A liquid filling process of the medical devices can be performed just before application. For example, a vessel occlusive device may be filled with a desired amount of saline solution before implanting the vessel occlusive device in a human body.

SUMMARY

A package system for a medical device is disclosed. The package system can be configured to contain the medical device in a storage state and provide a relatively elevated and stable holding platform to hold the medical device in an application state (e.g. in a liquid filling process of the medical device). The package system can also collect liquid in the application state. The package system can facilitate the handling of the medical device in the application state.

In some embodiments, the package system for a medical device may include a first part and a second part. The first part may include a holding platform configured to receive and hold at least a portion of the medical device in an application state of the medical device, and the second part may include contoured areas at least partially matching the medical device in a storage state of the medical device. In the application state, the first part and the second part can be assembled together, so that the holding platform in the first part can be in an elevated position relative to the second part.

In some embodiments, the first part may include a first leg portion, a middle portion and a second leg portion. In some embodiments, the holding platform may be integrated in the middle portion.

In some embodiments, the first part may further include a first hinge between the first leg portion and the middle portion, and a second hinge between the second leg portion and the middle portion. In some embodiments, the first leg portion and the second leg portion may be foldable along the first and second hinges. In some embodiments, the first leg portion and the second leg portion may be foldable toward under the holding platform when in use, so as to elevate the holding platform.

In some embodiments, the second part may include one or more pockets that may be configured to receive the first and second leg portions. In some embodiments, the second part may include a first pocket portion and a second pocket portion.

In some embodiments, the medical device may be a vessel occlusive device. In some embodiments, the medical device may include a portion configured as a vent during a liquid filling process of the medical device (e.g. a controller of a vessel occlusive device), and the holding platform may be configured to hold the portion.

In some embodiments, the package system may be configured to be positioned in an outer shell.

Other features and aspects of the systems, methods, and control concepts will become apparent by consideration of the following detailed description and accompanying drawings.

BRIEF DESCRIPTION OF THE DRAWINGS

Reference is now made to the drawings in which like reference numbers represent corresponding parts throughout.

DETAILED DESCRIPTION

For a medical device that may require a liquid filling process before application, the liquid filling process may be performed, for example, at an operation site. The liquid filling process can be cumbersome and may cause excess liquid to drain and/or spill onto tabletops and/or other working surfaces. Often, the liquid filling process requires a user to handhold the medical device while filling the medical device with a liquid. Improvements facilitating the liquid filling process, and preventing or at least reducing liquid spill may be desirable. It is to be appreciated that the embodiments as disclosed here can generally help improve the handling of the medical device when in use, and can be applicable to other procedures of handling the medical devices.

The embodiments as disclosed herein are directed to systems, methods and apparatuses configured to facilitate handling of a medical device (e.g. handling of the medical device in a liquid filling process). In some embodiments, when the medical device is in an application state, an apparatus may include a holding platform configured to hold the medical device, and a collection tray configured to support the holding platform and collect liquid spill. In some embodiments, the apparatus can be incorporated into a package system for the medical device. In some embodiments, the holding platform may be incorporated into a first part (e.g. a cover) of the package system for the medical device. In some embodiments, the collection tray may be incorporated into a second part (e.g. a container) of the package system for the medical device. In some embodiments, the first and second part of the package system may include contoured areas configured to accommodate contents of the medical device in a storage state. In some embodiments, when in the application state, the first part of the package system can be folded and fitted into one or more pockets of the second part of the package system, so that the first part of the package system can provide a relatively elevated and stable holding platform to hold the medical device. Holding the medical device in the elevated platform can help minimize movements of the medical device in the application state (e.g. a liquid filling process), free a user's hand, and help collect liquid spilled from the filling process.

References are made to the accompanying drawings that form a part hereof, and in which is shown by way of illustration of the embodiments in which the embodiments may be practiced. It is to be understood that the terms used herein are for the purpose of describing the figures and embodiments and should not be regarded as limiting the scope. The term "application state" can refer to a state when the medical device is being removed from a package and handled in use. An example of the application state may include, for example, when the medical device being filled with liquid. The term "storage state" refers to a state when the medical device (including accessories) is being stored, transported, or otherwise in a "packaged" state in a package system, when for example the package system is closed or sealed.

Figure 1:
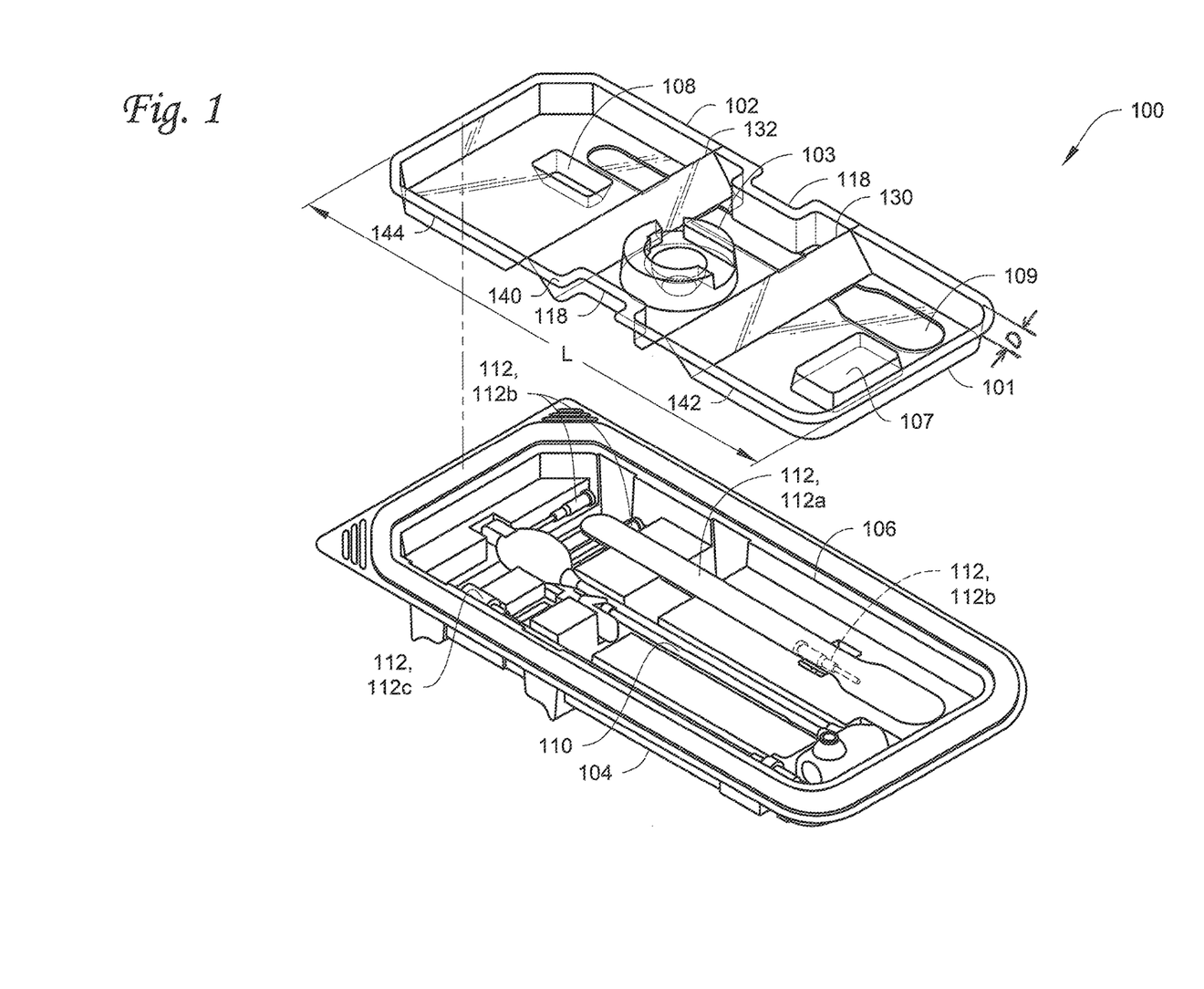
FIG. 1 illustrates a perspective view of a package system for a medical device, when the medical device is in a storage state.

Referring to FIG. 1, a package system 100 for a vessel occlusive device 110 and accessories 112, according to one embodiment, is disclosed. The package system 100 is configured to store the vessel occlusive device 110 and accessories 112 inside the package system 100 in a storage state. The vessel occlusive device 110 may require a liquid filling process before application. The package system 100 incorporates features configured to hold the vessel occlusive device 110 and/or accessories 112 in an application state (e.g. when the vessel occlusive device is removed from the package system 100 and being filled with liquid). The package system 100 also incorporates features configured to function as a collection tray to collect liquid spilled during the filling process.

It is to be noted that the vessel occlusive device 110 is used herein as an example to illustrate the embodiments. It is to be appreciated that the embodiments as disclosed herein are applicable to other suitable medical devices, particularly medical devices that may require a liquid filling process before application. It is to be appreciated that the embodiments as disclose herein generally improve the handling of the medical device and can be applicable to medical devices in procedures other than filling with liquid. The package system 100, in the illustrated embodiment, includes a first part 102 and a second part 104. The first part 102 and the second part 104 may have one or more contoured areas to accommodate the vessel occlusive device 110 and the accessories 112, so that the vessel occlusive device 110 and the accessories 112 may be held in the contoured areas of the package system 100 in the storage state. The accessories 112 can include, a measuring tape 112a, one or more needles 112b (e.g. non-coring needles), and an infusion tubing or set 112c. It is to be appreciated that the configurations (e.g. sizing) of the vessel occlusive device 110 and/or the contents of the accessories 112 may be varied in practice.

A profile of the first part 102 is configured to match an opening 106 of the second part 104, so that the first and the second parts 102, 104 can be fitted together. When the first part 102 and the second part 104 are fitted together, the first part 102 can be configured to cover the second part 104 and function as a cover for the second part 104, so that the contents in the second part 104 (e.g. the vessel occlusive device 110 and the accessories 112) are enclosed by the package system 100 (e.g. in the storage state).

In the illustrated embodiment, the first part 102 includes an extended portion 101 that can be fitted into the opening 106. As illustrated, the extended portion 101 may correspond to a recessed area of the first part 102. It is to be appreciated that this is exemplary. The first and second parts 102, 104 can be fitted by other suitable configurations. In some embodiments, the first and second parts 102, 104 can form, for example, a snap fit or a compression fit. In some embodiments, the first and/or second parts 102, 104 may include detents, which help mechanically engage the first and second parts 102, 104 together. In some embodiments, the first part 102 and the second part 104 can be nested together. The first part 102 can be, for example, nested in the second part 104 in some embodiments.

A holding platform 103 is integrated into the first part 102. The holding platform 103 can be, as illustrated, a contoured structure disposed on a middle portion 140 of the first part 102. The contoured structure of the holding platform 103 may be configured to hold and support the vessel occlusive device 110 in the application state. See FIG. 3 for the vessel occlusive device in the application state.

The first part 102 is generally divided into three portions by hinges (e.g. hinge lines) 130 and 132: a first leg portion 142, the middle portion 140, and a second leg portion 144 along a longitudinal direction defined by a length L. The first hinge 130 is defined between the first leg portion 142 and the middle portion 140, and the second hinge 132 is defined between the second leg portion 144 and the middle portion 140. The holding platform 103 is generally included in the middle portion 140 of the first part 102. The hinges 130 and 132 can facilitate folding of the first leg portion 142 and the second leg portion 144 relative to the middle portion 140 when in use.

It is to be appreciated that the first part 102 may include other features depending on the applications and the contents (e.g. the vessel occlusive device 110 and/or accessories 112) in the package system 100. For example, the first part 102 may include depressed or extruded areas 107, 108 and 109 that are configured to accommodate and hold the contents in the package system 100 in the storage state; including for example the vessel occlusive device 110 and/or the accessories 112, when the first and second parts 102, 104 are fitted together. The first part 102 may also include a finger grab portion(s) 118 to facilitate, for example, separating the first part 102 and the second part 104 by fingers.

Figure 2:
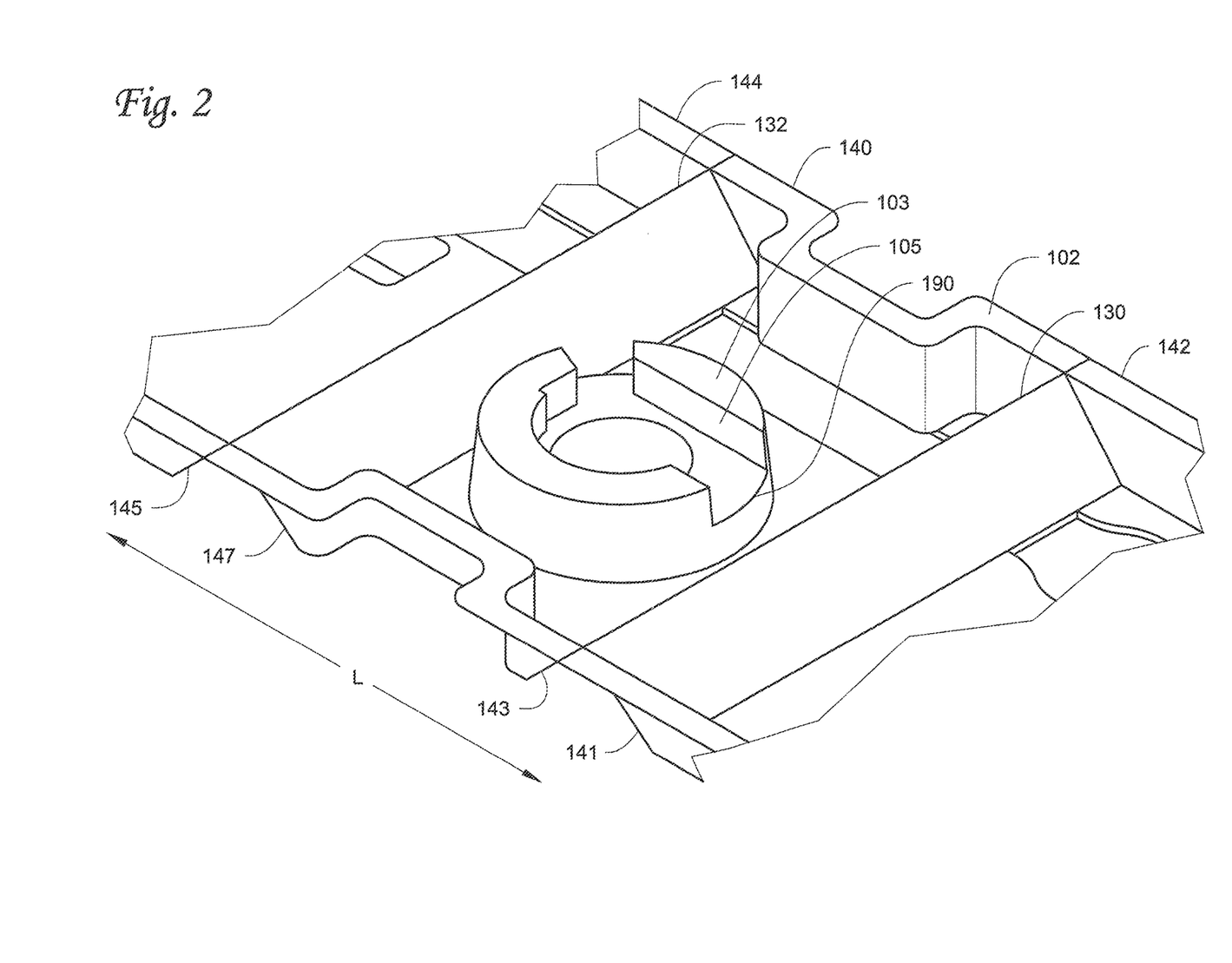
FIG. 2 illustrates a partial close-up view of a part of the package system, including a middle portion of the package system, as illustrated in FIG. 1.
Figure 3:
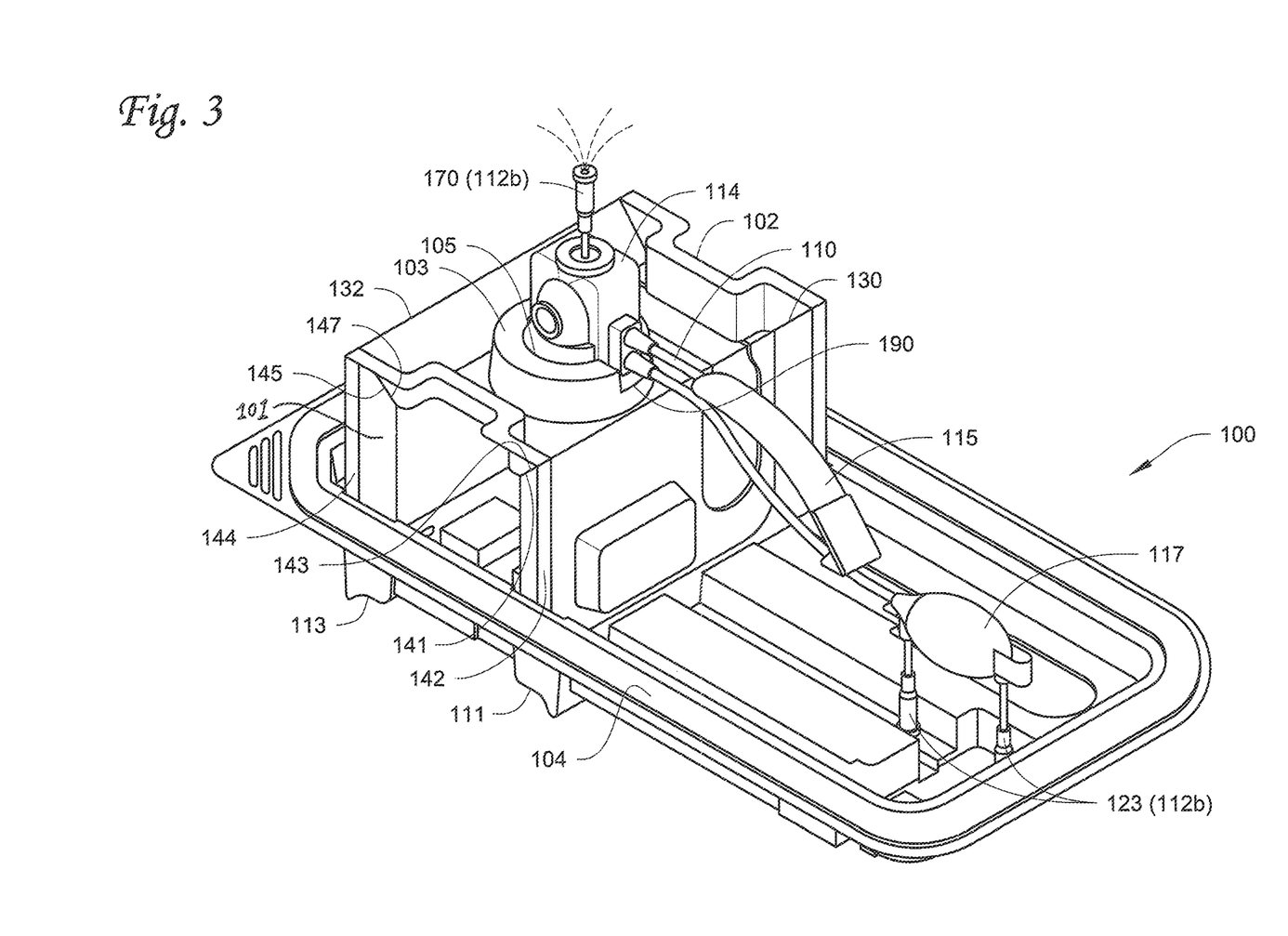
FIG. 3 illustrates a perspective view of the package system as illustrated in FIG. 1, when the medical device is in an application state.

Referring to FIGS. 2 and 3 together, an application of the package system 100 shown in FIG. 1 is illustrated. As illustrated in FIG. 2, the holding platform 103 is generally incorporated into the middle portion 140 of the first part 102.

Referring to FIGS. 1 and 2 together, the first and second leg portions 142, 144 extend laterally in the longitudinal direction defined by the length L of the first part 102. The first and second hinges 130 and 132 generally extend in a direction that traverses the longitudinal direction. Structurally, the first and second hinges 130 and 132 are generally more foldable/bendable than other regions of the first part 102, so that the first part 102 can be folded along the first and second hinges 130, 132. In some embodiments, the hinges 130 and 132 can be hinge lines or a structurally weakened region of the first part 102. Generally, the first part 102 has a relatively rigid structure, so that, for example, the first part 102 can function as a cover for the second part 104. When a force (e.g. from a user) is applied to the first part 102 to bend the first part, the relatively foldable/bendable hinges 130 and 132 are more likely to be bent compared to other portions of the first part 102. The first and second hinges 130 and 132 are configured to allow the first and second leg portions 142, 144 to be folded relative to the middle portion 140.

The holding platform 103 includes a holding structure 105, (e.g. a contoured holding pocket) that is configured to hold and support the vessel occlusive device 110 in the application state. It is to be appreciated that the holding structure 105 can be configured to generally accommodate a profile of at least a portion of the vessel occlusive device 110, so that the portion of the vessel occlusive device 110 can be received in the holding structure 105.

Referring to FIG. 3, the holding structure 105 of the holding platform 103 may be configured to accommodate a profile of a controller 114 of the vessel occlusive device 110, so that the vessel occlusive device 110 can be held and supported by the holding platform 103 in the application state. In some embodiments, the vessel occlusive device 110 may include portions that may not be held or supported by the holding structure 105. The holding structure 105 can still at least help keep a portion of the vessel occlusive device 110 in place. The controller 114 may be fitted into the holding structure 105 via a press fit, and/or one or more detents incorporated in the holding platform 103 or the controller 114.

It is to be appreciated that depending on the configuration of the vessel occlusive device 110, the holding structure 105 can also be configured to accommodate other portions of the vessel occlusive device 110. In the illustrated embodiment, the controller 114 of the vessel occlusive device 110 is designed to provide a vent during the liquid filling process, and liquid may spill during the liquid filling process. It may be advantageous to hold the controller 114 with the holding platform 103. It is to be appreciated that the holding platform 103 may be configured to hold other parts of the vessel occlusive device 110 or another device depending on different designs and/or applications.

In the orientation as shown in FIG. 3, the first and second leg portions 142 and 144 can be folded under the holding platform 103 along the hinge 130 and 132 respectively, when the first part 102 is in a folded configuration. At least some portion of the first and second leg portions 142 and 144 can be fitted into first and second pockets 111, 113 of the second part 104 in the folded configuration. The first and second pockets 111, 113 can have contoured structures configured to receive and accommodate at least some portion of the first and second leg portions 142, 144. In some embodiments, the first and second pockets 111, 113 may include detents to mechanically lock the first and second leg portions 142, 144 in place. The first and second pockets 111 and 113 can help hold the first and second leg portions 142 and 144 in place. The folded first and second leg portions 142 and 144 can help elevate the platform 103 relative to the second part 104, and may help make the holding platform 103 more accessible when in use.

Referring to FIGS. 2 and 3 together, the first leg portion 142 and the middle portion 140 have a first sloped side 141 and a second sloped side 143 along the hinge 130 respectively. The second leg portion 144 and the middle portion 102 have a third sloped side 145 and a fourth sloped side 147 respectively. When the first and second leg portions 142, 144 are folded along the first hinge 130 and the second hinge 132 respectively, the first and second sloped sides 141, 143 can move closer to each other, and the third and fourth sloped sides 145, 147 can move closer to each other respectively. When the sloped sides 141, 143, 145 and 147 get closer, the structure including the first and second leg portions 142, 144 and the elevated holding platform 103 can be relatively stable. The tension generated by folding the first and second leg portions 142, 144 and the relative stiffness of the first part 102 can help stabilize the folded configuration of the first part 102, when the first and second leg portions 142, 144 are held by first and second pockets 111, 113. Further, in some embodiments, the first sloped side 141 and the second sloped side 143 can meet with each other; and the third sloped side 145 and the fourth sloped side 147 can meet with each other. When the sloped sides 141, 143, 145 and 147 meet, the sloped sides 141, 143, 145 and 147 can rest on and support each other, stabilizing the folded configuration of the first part 102.

Referring to FIGS. 1 and 3 together, the sloped sides 141, 143, 145 and 147 are generally part of the extended portion 101 having a depth D. When the first part 102 is in the folded configuration, the first sloped side 141 may rest on the second sloped sides 143, and/or the third sloped side 145 can rest on the fourth sloped side 147. The depth D provides an area for the sloped sides 141, 143, 145 and 147 to rest on each other, and may help stabilize the folded configuration.

The depth D can also provide a supporting thickness for the first and second leg portions 142, 144 to allow the holding platform 103 to stand up.

In use, the package system 100 is opened and the first part 102 is separated from the second part 104, so that the contents (e.g. the vessel occlusive device 110 and accessories 112) of the package system 100 are exposed and accessible. The first and second leg portions 142, 144 of the first part 102 of the package system 100 can be folded along the hinges 130, 132 to the folded configuration. The folded first and second leg portions 142, 144 can be inserted into the first and second pockets 111, 113. It is to be noted that both of the first and second pockets 111, 113 can be configured to receive either the first or second leg portions 142, 144. When folded, the first and second leg portions 142, 144 can form a supporting structure for the holding platform 103.

When the first or second leg portions 142, 144 are inserted into the first and second pockets 111, 113 of the second part 104, the first sloped side 141 may rest on the second sloped sides 143, and the third sloped side 145 may rest on the fourth sloped side 147. The folded first and second leg portions 142, 144 can provide a relatively elevated structure relative to the second part 104 and help make the holding platform 103 accessible. It is to be appreciated that the first and second sloped sides 141, 143, and the third and fourth sloped sides 145, 147 do not need to meet with each other in the folded configuration.

In the illustrated embodiment, the controller 114 of the vessel occlusive device 110 can be received by the holding structure 105, which helps holding the vessel occlusive device 110 in place and minimize the movements of the vessel occlusive device 110 in the application state. Some other parts of the vessel occlusive device 110, such as for example, an occlusive tape 115 and a pressure compensator 117, are allowed to hang from the controller 114. Holding the vessel occlusive device 110 by the holding structure 105 can free a user's hand, facilitating handling of the vessel occlusive device 110. The user's hand can be used to handle, for example, infusing the occlusive tape 115 with a liquid through one or more infusion needles 123 (e.g. 112b).

In the illustrated embodiments, the occlusive tape 115 and the pressure compensator 117 are both attached to the controller 114. Referring to FIGS. 2 and 3, the holding structure 105 includes a recess 190 to accommodate the occlusive tape 115 and the pressure compensator 117. The recess 190 allows clearance for the occlusive tape 115 and the pressure compensator 117.

In a liquid filling process, a user can connect a liquid filled syringe (not shown) to one or more the infusion tubes 123 (e.g. 112b). The liquid from the syringe can be filled into the occlusive tape 115 through the controller 114. A needle 170 (e.g. 112b) can be inserted into the controller 114 to function as a vent in the liquid filling process of the vessel occlusive device 110 (e.g. a saline solution), so that air displaced by the liquid can escape. When the occlusive tape is filled with the liquid, the liquid can come out from the needle 170. The spilled liquid can be collected by the second part 104 of the package system 100.

In the illustrated embodiment, the controller 114 is the portion of the vessel occlusive device 110 that may spill liquid during the liquid filling process. This is exemplary. It is to be appreciated that the holding platform 103 may be generally configured to hold a portion of a medical device that may spill liquid during a liquid filling process. When a portion of the medical device includes a vent, for example, the liquid may spill through the vent during the liquid filling process as the air being displaced by the liquid. Therefore, the portion with a vent may be a good candidate to be held by the holding platform 103. It is to be understood that other portions of the medical device can also be held by the holding platform 103.

It is to be appreciated that the package system 100 can be made from a thermal plastic, such as for example, acrylonitrile butadiene styrene (ABS), polyester copolymer (PETG), polystyrene (PS), polycarbonate (PC), or polypropylene (PP), metal or other suitable materials. In some embodiments, the package system 100 can be made from a transparent material. In some embodiments, the package system 100 can be made using a vacuum forming operation. In some embodiments, the package system 100 can be made using injection, blow and/or rotational molding, or other thermal processes.

Figure 4:
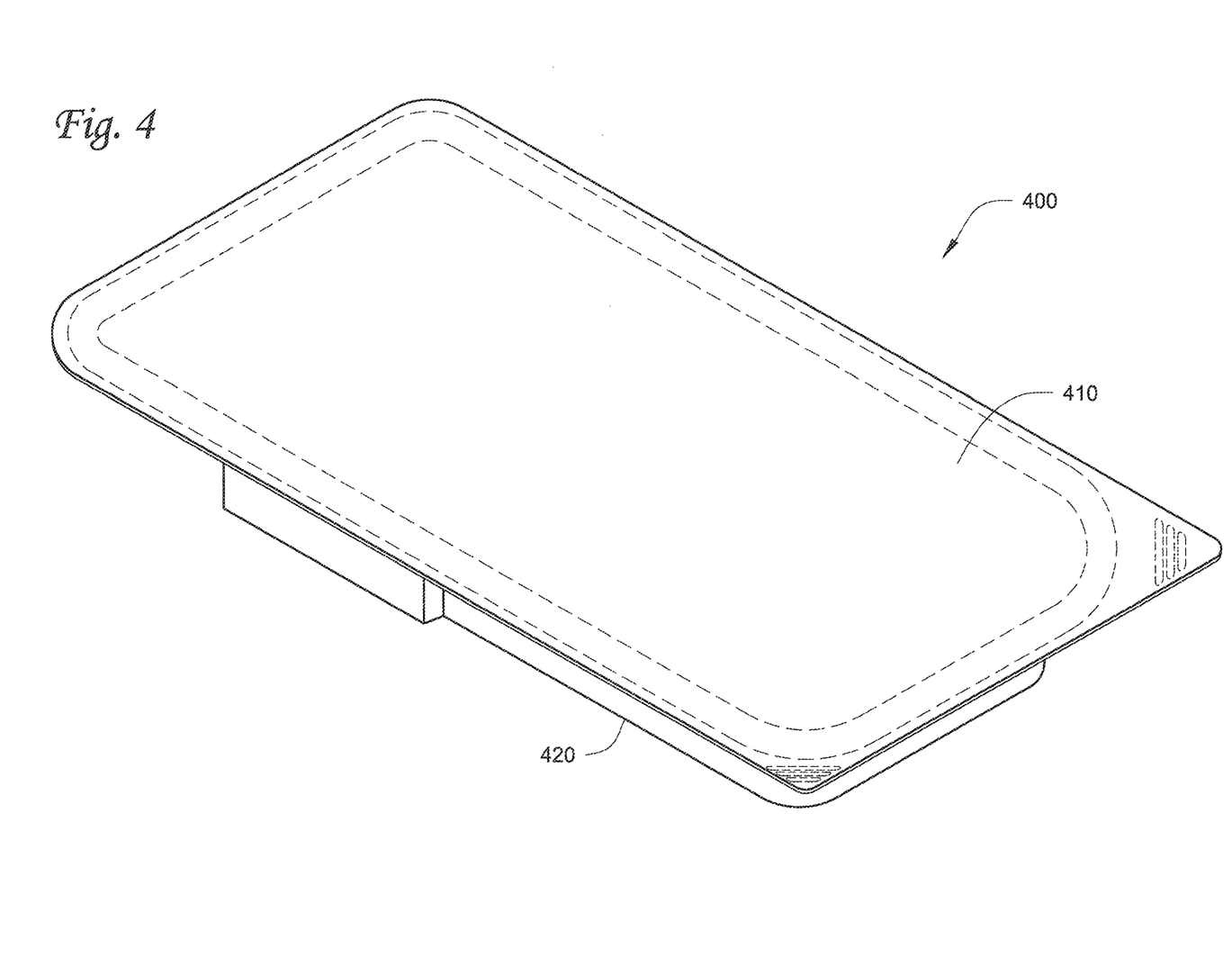
FIG. 4 illustrates a perspective view of an outer shell system, according to one embodiment.
Figure 5:
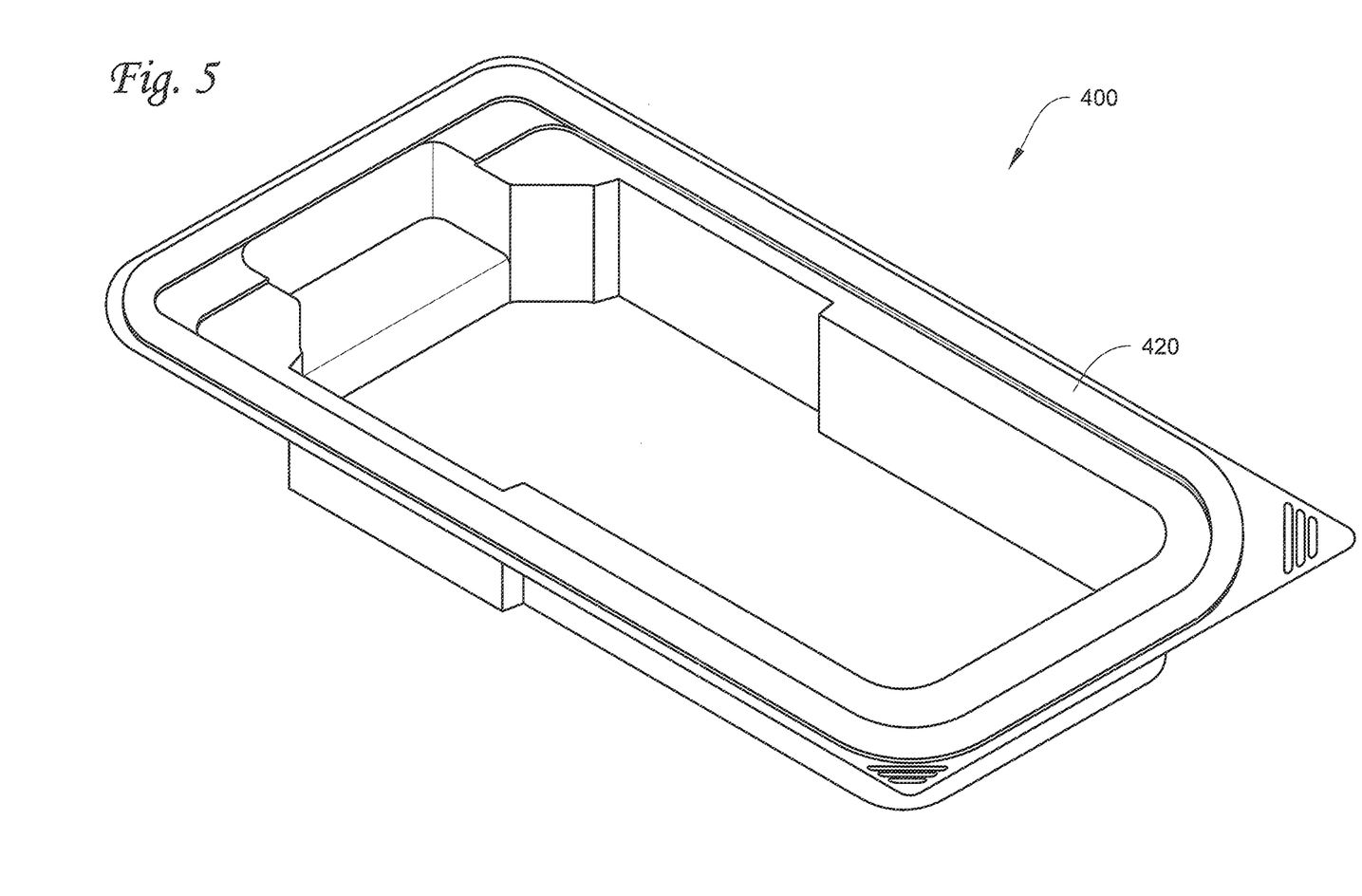
FIG. 5 illustrates a perspective view of a portion of the outer shell system as shown in FIG. 4.

Referring to FIGS. 4 and 5, an outer shell 400 for the package system as described herein (e.g. the package system 100) is illustrated. The package system can be, for example, sealed in the outer shell 400, which may, for example, help provide protection to the package system, and may help keep the package system sterilized.

In the illustrated embodiment, the outer shell 400 includes a cover 410 and a container 420, where the cover 410 can be configured to be attachable to and cover the container 420. Referring to FIG. 5, the container 420 can include contoured areas configured to match, for example, a profile of the package system 100. The package system 100 can be received and nested in the container 420. hen the package system 100 is received in the container 420, the contoured areas can help minimize movement of the package system 100.

In use, the cover 410 of the outer shell 400 is removed, so that the package system included in the outer shell 400 can be accessed.

In some embodiments, the cover 410 may be made of a membrane of porous spun polyolefin fibers, such as Tyvek®, which may be thermally bond to the container 420. In some embodiments, the cover 410 may also be a thermo plastic, and the cover 410 may be suitably mechanically bond to the container 420, for example, by thermal or adhesive bonding.

It is to be appreciated that, in some embodiments, the holding platform and the collection tray may be provided separately form a package system for a medical device.

ASPECTS

Any of aspects 1 to 8 may be combined with any of aspects 9 to 16.
Aspect 1. A package system for a medical device, comprising:
a first part; and
a second part,
wherein the first part includes a holding platform configured to receive and hold at least a portion of the medical device in an application state of the medical device,
the second part includes contoured areas at least partially matching a profile of the medical device in a storage state of the medical device, and
the first part and the second part are configured to be assembled together in the application state so that the holding platform is at an elevated position relative to the second part.
Aspect 2. The package system of aspect 1, wherein the medical device is a vessel occlusive device.
Aspect 3. The package system of any of aspects 1 and 2, wherein the first part includes a first leg portion, a middle portion and a second leg portion, and the holding platform is integrated in the middle portion.
Aspect 4. The package system of any of aspects 1 to 3, wherein the first part further includes a first hinge between the first leg portion and the middle portion, and a second hinge between the second leg portion and the middle portion.
Aspect 5. The package system of any of aspects 3 and 4, wherein the first leg portion and the second leg portion are foldable toward under the holding platform.
Aspect 6. The package system of any of aspects 3 to 5, wherein the second part includes one or more pockets, and the one or more pockets are configured to receive the first and second leg portions.
Aspect 7. The package system of any of aspects 2 to 6, wherein the medical device includes a portion configured as a vent during a liquid filling process of the medical device, and the holding platform is configured to hold the portion.
Aspect 8. The package system of any of aspects 1-8, wherein the package system is configured to be positioned in an outer shell.
Aspect 9. A medical device package, comprising:
a medical device; and
a package system, wherein the package system includes
a first part ; and
a second part,
wherein the first part includes a holding platform configured to receive and hold
at least a portion of the medical device in an application state of the medical device, and
the second part includes contoured areas at least partially mating a profile of the medical device in a storage state of the medical device, and
the first part and the second part are configured to be assembled together in the application state so that the holding platform is at an elevated position relative to the second part.
Aspect 10. The medical device package of aspect 9, wherein the medical device is a vessel occlusive device.
Aspect 11. The medical device package of any of aspects 9 and 10, wherein the first part includes a first leg portion, a middle portion and a second leg portion, and the holding platform is included in the middle portion.
Aspect 12. The medical device package of any of aspects 9 to 11, wherein the first part further includes a first hinge between the first leg portion and the middle portion, and a second hinge between the second leg portion and the middle portion.
Aspect 13. The medical device package of any of aspects 11 and 12, wherein the first leg portion and the second leg portion are foldable toward under the holding platform.

Aspect 14. The medical device package of any of aspects 11 to 13, wherein the second part includes one or more pockets, and the one or more pockets are configured to receive the first and second leg portions.

Aspect 15. The medical device package of any of aspects 10 to 14, wherein the medical device includes a part configured as a vent during a liquid filling process of the medical device, and the holding platform is configured to hold the part.

Aspect 16. The medical device package of any of aspects 9 to 15, wherein the package system is configured to be positioned in an outer shell.

With regard to the foregoing description, it is to be understood that changes may be made in detail, without departing from the scope of the present invention. It is understood that the specification and depicted embodiments are to be considered exemplary only, with a true scope and spirit of the invention being indicated by the broad meaning of the claims.

What claimed is:

1. A package system for a medical device, comprising:
a first part including a first leg portion, a middle portion, and a second leg portion; and
a second part,
wherein the first part includes a holding platform configured to receive and hold at least a portion of the medical device in an application state of the medical device, wherein the holding platform is integrated in the middle portion, the holding platform including a holding structure that is contoured to receive the portion of the medical device in the application state, the holding structure including a recess that provides clearance for a portion of the medical device that extends beyond the holding structure in the application state, the holding structure being formed on a side of the first part that faces away from the second part when in a storage state of the medical device,
the second part includes contoured areas at least partially matching a profile of the medical device in the storage state of the medical device, and
the first part and the second part are configured to be assembled together in the application state so that the holding platform is at an elevated position relative to the second part.

2. The package system of claim 1, wherein the first part further includes a first hinge between the first leg portion and the middle portion, and a second hinge between the second leg portion and the middle portion.

3. The package system of claim 1, wherein the first leg portion and the second leg portion are foldable toward an underside of the holding platform.

4. The package system of claim 1, wherein the second part includes one or more pockets, and the one or more pockets are configured to receive the first and second leg portions.

5. The package system of claim 1, wherein the package system is configured to be positioned in an outer shell.

6. A medical device package, comprising:
a medical device; and
a package system, wherein the package system includes
a first part including a first leg portion, a middle portion, and a second leg portion; and
a second part,
wherein the first part includes a holding platform configured to receive and hold at least a portion of the medical device in an application state of the medical device, wherein the holding platform is integrated in the middle portion, the holding platform including a holding structure that is contoured to receive the portion of the medical device in the application state, the holding structure including a recess that provides clearance for a portion of the medical device that extends beyond the holding structure in the application state, the holding structure being formed on a side of the first part that faces away from the second part when in a storage state of the medical device, and
the second part includes contoured areas at least partially matching a profile of the medical device in the storage state of the medical device, and
the first part and the second part are configured to be assembled together in the application state so that the holding platform is at an elevated position relative to the second part.

7. The medical device package of claim 6, wherein the medical device is a vessel occlusive device.

8. The medical device package of claim 6, wherein the first part further includes a first hinge between the first leg portion and the middle portion, and a second hinge between the second leg portion and the middle portion.

9. The medical device package of claim 6, wherein the first leg portion and the second leg portion are foldable toward an underside of the holding platform.

10. The medical device package of claim 6, wherein the second part includes one or more pockets, and the one or more pockets are configured to receive the first and second leg portions.

11. The medical device package of claim 7, wherein the medical device includes a part configured as a vent during a liquid filling process of the medical device, and the holding platform is configured to hold the part.

12. The medical device package of claim 6, wherein the package system is configured to be positioned in an outer shell.

13. The package system of claim 1, wherein when in the application state, the first leg portion and the second leg portion are folded toward an underside of the holding platform and are inserted into one or more pockets of the second part.

14. The medical device package of claim 6, wherein when in the application state, the first leg portion and the second leg portion are folded toward an underside of the holding platform and are inserted into one or more pockets of the second part.

* * * * *